(12) United States Patent
Yang et al.

(10) Patent No.: US 8,034,985 B2
(45) Date of Patent: Oct. 11, 2011

(54) CATALYST FOR THE SYNTHESIS OF $CF_3CF_2I$

(75) Inventors: Shuwu Yang, Williamsville, NY (US); HsuehSung Tung, Getzville, NY (US)

(73) Assignee: Honeywell International, Ltd., Morristown, NJ (US)

( * ) Notice: Subject to any disclaimer, the term of this patent is extended or adjusted under 35 U.S.C. 154(b) by 0 days.

(21) Appl. No.: 11/706,776

(22) Filed: Feb. 15, 2007

(65) Prior Publication Data

US 2008/0200735 A1    Aug. 21, 2008

(51) Int. Cl.
*C07C 19/07*   (2006.01)
(52) U.S. Cl. .................................. 570/174; 570/170
(58) Field of Classification Search .............. 570/170, 570/174
See application file for complete search history.

(56) References Cited

U.S. PATENT DOCUMENTS

| | | | |
|---|---|---|---|
| 2,920,111 A * | 1/1960 | Braid et al. ................... | 570/163 |
| 3,002,030 A * | 9/1961 | Hauptschein et al. ......... | 570/174 |
| 3,052,732 A * | 9/1962 | Krespan ........................ | 570/174 |
| 3,072,730 A * | 1/1963 | Twelves ........................ | 570/164 |
| 3,076,041 A * | 1/1963 | Twelves et al. ............... | 570/174 |
| 3,201,483 A * | 8/1965 | Davis ............................ | 570/170 |
| 3,351,671 A * | 11/1967 | Anello et al. .................. | 570/170 |
| 3,429,938 A * | 2/1969 | Foulletier ...................... | 570/161 |
| 3,644,544 A * | 2/1972 | Cammarata et al. .......... | 570/170 |
| 3,755,474 A * | 8/1973 | Bjorson ........................ | 570/170 |
| 4,748,282 A * | 5/1988 | Bargigia et al. ............... | 568/842 |
| 4,794,200 A * | 12/1988 | Tordeux et al. ............... | 570/170 |
| 5,254,775 A * | 10/1993 | Holloway et al. ............. | 570/170 |
| 5,892,136 A * | 4/1999 | Nagasaki et al. .............. | 570/174 |
| 6,680,044 B1 * | 1/2004 | Tonkovich et al. ........... | 423/652 |
| 6,946,582 B2 * | 9/2005 | Katsube et al. ............... | 570/174 |
| 6,977,316 B1 * | 12/2005 | Mukhopadhyay et al. ... | 570/174 |
| 7,009,083 B2 * | 3/2006 | Pennetreau et al. .......... | 570/168 |
| 7,071,367 B1 * | 7/2006 | Mukhopadhyay et al. ... | 570/101 |
| 7,196,236 B2 * | 3/2007 | Mukhopadhyay et al. ... | 570/174 |
| 2006/0122440 A1 * | 6/2006 | Mukhopadhyay et al. ... | 570/152 |
| 2008/0108854 A1 * | 5/2008 | Yang et al. .................... | 570/174 |

FOREIGN PATENT DOCUMENTS

| | | |
|---|---|---|
| FR | 2794456 | 12/2000 |
| JP | 52068110 | 6/1977 |
| JP | 2005/008543 | 1/2005 |
| KR | 20040043774 | 5/2004 |

OTHER PUBLICATIONS

Periodic Table of Elements. Hayden U Azul 1987.*
Nagasaki et al., "*Study on a novel catalytic reaction and its mechanism for $CF_3I$ synthesis*"; Catal. Today; 88 (2004) 121-126.
Nagasaki et al.; "*The development of a novel catalytic technology for $CF_3I$ manufacture*"; Proceedings of the Halon Options Technical Working Conference, Albuquerque, NM; Jun. 2000; pp. 180-185.
N. Nagasaki; "*A novel catalytic technology for the manufacture of $CF_3I$*"; Specialty Chemicals Magazine; Jun. 2002; pp. 31-32.
Lee et al.; "*Synthesis of $CF_3I$ by direct iodination of $CF_3COOH$ on solid catalyst*"; Hwahak Konghak 39(2); (2001); pp.
Nature (London, United Kingdom), 166, pp. 192-193 (1950).
J. Chem, Soc., pp. 584-585 (1951).

* cited by examiner

*Primary Examiner* — Sudhakar Katakam
(74) *Attorney, Agent, or Firm* — Bruce O. Bradford

(57) ABSTRACT

A process for the preparation of a fluoroiodoalkane compound represented by the formula: $CF_3(CF_2)_n$—Y, wherein n is 0 or 1. The process includes contacting A, B and C. A is represented by the formula: $CF_3(CF_2)_n$—Y, wherein n is 0 or 1, and Y is selected from the group consisting of: H, Cl, Br, and COOH. B is a source of iodine, and C is a catalyst containing elements with $d^1s^1$ configuration and lanthanide elements. The process occurs at a temperature, and for a contact time, sufficient to produce the fluoroiodoalkane compound.

17 Claims, No Drawings

CATALYST FOR THE SYNTHESIS OF $CF_3CF_2I$

BACKGROUND OF THE INVENTION

1. Field of the Invention

The present disclosure is related to the synthesis of $CF_3I$ and $CF_3CF_2I$. More particularly, the present disclosure is related to a family of catalysts used in the synthesis of $CF_3I$ and $CF_3CF_2I$.

2. Description of Related Art

Trifluoroiodomethane ($CF_3I$) and pentafluoroiodoethane ($C_2F_5I$) are useful chemicals. $CF_3I$ is a potential fire extinguisher substituting for trifluorobromomethane, a fluorine-containing intermediate compound for introducing a trifluoromethyl group in producing surfactants, chemicals and pharmaceuticals, and a refrigerant with low global warming potential when blended together with some hydrofluorocarbons. $C_2F_5I$ is used as a synthesis intermediate in many applications related to the field of fluorinated surface-active substances, and more particularly, as bases for fire-extinguishing formulations, as hydrophobic and olephobic finishes on various substrates, and as a medical agent.

Both batch and continuous processes have been developed for the production of trifluoroiodomethane. For batch process, it has been shown that trifluoroiodomethane can be prepared by reacting trifluoroacetic acid or its derivative with iodine. However, this process required strict control of reaction conditions and moisture level in source materials, and moreover, expensive silver trifluoroacetate had to be used in order to achieve a high yield of trifluoroiodomethane.

Alternatively, trifluoroiodomethane can be made through continuous vapor-phase reaction. However, the catalyst families developed so far for known processes are limited to supported salts of alkali and alkaline earth metals and CuI. These catalysts suffered from rapid deactivation due to carbon formation during reaction and/or the loss and sintering of active components in catalysts.

Accordingly, there is a need to develop alternative catalyst systems and processes that overcome, alleviate, and/or mitigate one or more of the aforementioned and other deleterious effects of the prior art catalysts and processes.

SUMMARY OF THE INVENTION

The present disclosure provides a process for the preparation of a fluoroiodoalkane compound represented by the formula: $CF_3(CF_2)_n$—Y, wherein n is 0 or 1. The process includes the step of contacting A, B and C, wherein A is represented by the formula: $CF_3(CF_2)_n$—Y, wherein n is 0 or 1, and Y is selected from the group consisting of: H, Cl, Br, and COOH. B is a source of iodine, and C is a catalyst containing elements with $d^1s^1$ configuration and lanthanide elements. The process occurs at a temperature, and for a contact time, sufficient to produce the fluoroiodoalkane compound.

It is an object of the present disclosure to provide a process for producing trifluoroiodomethane ($CF_3I$) and pentafluoroiodoethane ($C_2F_5I$) using elements with a $d^1s^1$ configuration or lanthanide elements as a catalyst.

It is another object of the present disclosure to provide a process for producing trifluoroiodomethane ($CF_3I$) and pentafluoroiodoethane ($C_2F_5I$) using transition metals, noble metals, or rare earth metals as promoters for the activity of the catalysts of the present disclosure.

The above-described and other features and advantages of the present disclosure will be appreciated and understood by those skilled in the art from the following detailed description and appended claims.

DETAILED DESCRIPTION OF THE INVENTION

The present disclosure provides catalysts used in a process to prepare a fluoroiodoalkane compound represented by the formula: $CF_3(CF_2)_n$—I, where n is 0 or 1, from a compound represented by the formula: $CF_3(CF_2)_n$—Y, wherein Y is selected from H, Cl, Br, and COOH, and n is 0 or 1. The process can be executed in the presence of a source of iodine ($I_2$, HI, ICl, $IF_5$, $Cl_4$, etc.), and in the presence or absence of a source of oxygen ($O_2$, air, ozone, $N_2O$, $H_2O_2$, etc.).

In some embodiments, catalysts for this process contain elements with $d^1s^1$ configuration and/or lanthanide elements, including but not limited to, Scandium (Sc), Yttrium (Y), Lanthanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb) and Lutetium (Lu), in any existing forms of any existing precursors.

Catalysts can be prepared by supporting each of the elements or a mixture thereof, on a support, preferably activated carbon, or used directly as bulk (unsupported). The amount of these elements ranges from 0.001% to 100% by weight of the entire catalyst, and all the subranges therebetween. Precursors of these elements can be oxide, nitrate, halide, carbonate, bicarbonate, sulfate and phosphate, or other existing salts and compounds.

Catalysts can be used by themselves or can be promoted/modified by transition metal (including noble metal) or main group elements. Transition metal promoters/modifier includes, but is not limited to, the following elements: Ti, V, Cr, Mn, Co, Ni, Zn, Zr, Nb, Mo, Ru, Rh, Pd, W, Re, Pt, Ag, Ce, Pr, etc. Any combination of these elements, or a salt or other form of one or a combination of these elements is included in the list of promoters/modifiers. Promoters/modifier of main group elements includes, but not limited to, the following: alkali metal (Li, Na, K, Rb and Cs), alkaline earth metal (Be, Mg, Ca, Sr and Ba), Al, P, Ga, In, Sn, Sb, Tl, Bi, etc, and any combination of these elements. The promoter/modifier can be a single element in any existing forms of any existing precursors (i.e., a salt), or a combination of any existing forms of any existing precursors of those elements.

In some embodiments, when alkali and/or alkaline earth metals are used as promoter/modifier, the atomic ratio of elements with $d^1s^1$ configuration and lanthanide elements to these metals is greater than 1, that is, only small amounts of alkali and/or alkali earth metals are used as a promoter. For other promoter/modifier, the atomic ratio of elements with $d^1s^1$ configuration and lanthanide to promoters/modifiers in a catalyst ranges from 0.00001 to 100000, more preferably from 0.0001 to 10000. The above ranges provided for the atomic ratio of elements include all subranges that fall within the parameters of the ranges identified.

The as-prepared promoted catalysts can be calcined in an inert gas such as nitrogen at 100-750° C., more preferably at 300-600° C., and all subranges therebetween.

Before reaction, the catalysts can be further treated in an inert gas, hydrogen, HF, HCl, $H_1$, $F_2$, $Cl_2$, $CF_3H$, $I_2$, air, oxygen, or a mixture thereof, at, above, or below the particular reaction temperature in which they will be used. The reaction temperature ranges can be from about 100° C. to about 750° C., and all temperatures therebetween. More preferably, the reaction temperature ranges from about 300° C. to about 600° C., and all temperatures therebetween.

In the practice of the process of the present disclosure, the reaction can be carried out at a temperature from about 100° C. to about 750° C., at a pressure from about 0.001 atm to about 100 atm, and for a contact time from about 0.001 sec to about 300 hours. The contact time is defined as volume of catalyst divided by the volumetric velocity of all feeds. Also, the reaction can be carried out under pressures and a contact duration that fall within those ranges.

The process can be either a batch process or it can be a continuous process. Also, the reactor type can be a fixed bed reactor or a moving bed reactor, such as fluidized bed reactor, rotary reactor, rising bed reactor, or a combination thereof.

The reactor can optionally include a diluent, including an inert gas such as nitrogen, CO, $CO_2$, water, an organic solvent, or a mixture thereof.

The process can further include one or more of the following steps: passing the fluoroiodoalkane, which can be trifluoromethyl iodide or pentafluoroethyl iodide, through a scrubber containing an aqueous alkali solution. The process can also include passing the fluoroiodoalkane through a scrubber containing a drying agent, followed by cooling at a temperature below the boiling temperature of the fluoroiodoalkane to condense. The process can also include a step of isolating the fluoroiodoalkane from the reaction mixture in essentially a pure form.

The following non-limiting examples are illustrative of the various embodiments of the present disclosure. It is within the ability of a person of ordinary skill in the art to select other variables from amongst the many known in the art without departing from the scope of the present disclosure. Accordingly, these examples shall serve to further illustrate the present disclosure, not to limit it.

EXAMPLE 1

Catalyst preparation—Preparation of carbon supported lanthanum oxide or salt ($La_2O_3$/C) catalysts: Designated amount of $La(NO_3)_3$ was dissolved in deionized water (the amount of water was calculated from the pore volume of a support). After $La(NO_3)_3$ was dissolved completely, designated amount of activated carbon (pre-dried at 100-120° C. for 12 hrs) was slowly poured into the solution, or vice versa. The paste was stirred continuously to achieve homogeneous impregnation and then was put in the hood overnight to allow adequate impregnation. Subsequently, the impregnated sample was dried in an oven at 100-120° C. for 12 hrs and calcined at 450-550° C. for 4 hrs in flowing nitrogen.

Preparation of promoted $La_2O_3$/C catalysts: Designated amount of $La(NO_3)_3$ and designated amount of precursor of a promoter were dissolved in desired amount of deionized water. After all salts were dissolved completely, designated amount of activated carbon (pre-dried at 100-120° C. for 12 hrs) was slowly poured into the solution, or vice versa. The paste was stirred continuously to achieve homogeneous impregnation and then was put in the hood overnight to allow adequate impregnation. Subsequently, the impregnated sample was dried in an oven at 100-120° C. for 12 hrs and calcined at 450-550° C. for 4 hrs in flowing nitrogen. In case of step-wise impregnation, a salt of a promoter was first impregnated on activated carbon overnight. After drying/calcination, $La(NO_3)_3$ was impregnated on activated carbon, followed by drying and calcination.

The activated carbon support used in this disclosure was pelletized Shirasagi C2X 4/6-2 from Japan EnviroChemicals, Ltd, although any support known in the art could be used. Pelletized Shirasagi C2X 4/6-2 is highly purified, with a surface area above 1000 $m^2$/g and an average pore diameter 23 Å.

EXAMPLE 2

Reactivity of carbon supported catalysts containing elements with $d^1s^1$ configuration—Table 1 lists the activity and selectivity of some activated carbon supported catalysts which contain elements with $d^1s^1$ configurations, such as Scandium (Sc), Yttrium (Y), and Lanthanum (La), after 20 hrs on stream at 500° C. For 5% $Sc_2O_3$/C, it began to show activity after 7 hours on stream. The $CF_3H$ conversion and $CF_3I$ selectivity of 5% $Sc_2O_3$/C were 6.3% and 65.5%, respectively, after 10 hrs on steam. The catalyst remained stable after 20 hrs on stream, with 6.2% $CF_3H$ conversion, 65.4% $CF_3I$ selectivity and 1.6% $CF_3CF_2I$ selectivity. The induction period was 12 hrs for 5% $Y_2O_3$/C, which exhibited 4.6% $CF_3H$ conversion and 65.5% $CF_3I$ selectivity after reacted for 20 hrs. For 5% $La_2O_3$/C, its induction period was 8 hrs. At 10 hrs of reaction time, it showed 8.3% $CF_3H$ conversion and 65.0% $CF_3I$ selectivity. Its activity increased to about 10% after 12 hrs on stream and then remained stable thereafter. After reacted for 20 hrs, the $CF_3H$ conversion, $CF_3I$ selectivity and $CF_3CF_2I$ selectivity of 5% $La_2O_3$/C were 10.3%, 64.9% and 2.5%, respectively.

TABLE 1

Reactivity of carbon supported catalysts containing elements with $d^1s^1$ configuration. Reaction condition: 500° C., $I_2/CF_3H$ = 0.33, $O_2/CF_3H$ = 0.1, contact time: 20 s. Reaction time: 20 hr.

| Catalyst | $CF_3H$ conversion (%) | $CF_3I$ selectivity (%) | $CF_3CF_2I$ selectivity (%) |
|---|---|---|---|
| 5% $Sc_2O_3$/C | 6.2 | 65.4 | 1.6 |
| 5% $Y_2O_3$/C | 4.6 | 65.5 | 1.5 |
| 5% $La_2O_3$/C | 10.3 | 64.9 | 2.5 |

EXAMPLE 3

Reactivity of carbon supported catalysts containing lanthanide (rare-earth) elements. The reactivity of carbon supported catalysts containing various lanthanide (rare-earth) elements are listed in Table 2. The data given here was obtained after 10 hrs on stream. The catalysts contained 10 wt. % of rare earth metal oxide were tested at 500° C., and they showed about 6-12% $CF_3H$ conversion, about 65% $CF_3I$ selectivity and about 2-3% $CF_3CF_2I$ selectivity. 10% $La_2O_3$/C exhibited 11.9% $CF_3H$ conversion, which was slightly greater than the other catalysts. 5% $Eu_2O_3$/C and 5% $Tm_2O_3$/C were tested at 550° C. in order to reduce the induction period. The $CF_3H$ conversion, $CF_3I$ selectivity and $CF_3CF_2I$ selectivity for 5% $Eu_2O_3$/C were 34.0%, 57.7% and 4.8%, respectively, and those for 5% $Tm_2O_3$/C were 34.9%, 60.4% and 3.7%, respectively.

TABLE 2

Reactivity of carbon supported catalysts containing lanthanide (rare-earth) elements. Reaction condition: 500 or 550° C., $I_2/CF_3H$ = 0.33, $O_2/CF_3H$ = 0.1, contact time: 20 s. Reaction time: 10 hr.

| Catalyst | Reaction temp. (° C.) | $CF_3H$ conversion (%) | $CF_3I$ selectivity (%) | $CF_3CF_2I$ selectivity (%) |
|---|---|---|---|---|
| 10% $La_2O_3$/C | 500 | 11.9 | 65.1 | 2.3 |
| 10% $Pr_2O_3$/C | 500 | 10.7 | 64.6 | 2.7 |
| 10% $Sm_2O_3$/C | 500 | 9.7 | 64.9 | 2.4 |

TABLE 2-continued

Reactivity of carbon supported catalysts containing lanthanide
(rare-earth) elements. Reaction condition: 500 or 550° C., $I_2/CF_3H = 0.33$,
$O_2/CF_3H = 0.1$, contact time: 20 s. Reaction time: 10 hr.

| Catalyst | Reaction temp. (° C.) | $CF_3H$ conversion (%) | $CF_3I$ selectivity (%) | $CF_3CF_2I$ selectivity (%) |
|---|---|---|---|---|
| 10% $Er_2O_3$/C | 500 | 7.6 | 65.3 | 2.0 |
| 10% $Yb_2O_3$/C | 500 | 6.2 | 65.6 | 1.6 |
| 5% $Eu_2O_3$/C | 550 | 34.0 | 57.7 | 4.8 |
| 5% $Tm_2O_3$C | 550 | 34.9 | 60.4 | 3.7 |

EXAMPLE 4

Effect of $La_2O_3$ loading on the reactivity of $La_2O_3$/C. The effect of $La_2O_3$ loading on the catalyst activity and selectivity was investigated and the data is listed in Table 3. When there was no lanthanum oxide, the activated carbon support itself was not active at 500° C. Only trace amount (0.06%) of $CF_3H$ was converted into $CF_3I$ and some other products. However, when only 2 wt. % $La_2O_3$ was supported on carbon, the catalyst gave 12.8% $CF_3H$ conversion and 64.8% $CF_3I$ selectivity. When the $La_2O_3$ loading was increased to 5 wt. %, the catalyst activity exhibited slightly lower activity (8.3% $CF_3H$ conversion) after 10 hrs on stream. With increasing $La_2O_3$ loading from 5 wt. % to 20 wt. %, the $CF_3H$ conversion increased monotonically from 8.3% to 12.9%, with slightly drop of $CF_3I$ selectivity from about 65% to about 62%. The $CF_3CF_2I$ selectivity of these $La_2O_3$/C catalysts was between 2% to 4%.

TABLE 3

Effect of $La_2O_3$ loading on the reactivity of $La_2O_3$/C. Reaction
condition: 500° C. $I_2/CF_3H = 0.33$, $O_2/CF_3H = 0.1$, contact time:
20 s. Reaction time: 10 hr.

| $La_2O_3$ loading (wt. %) | $CF_3H$ conversion (%) | $CF_3I$ selectivity (%) | $CF_3CF_2I$ selectivity (%) |
|---|---|---|---|
| 0 (carbon-only) | 0.06 | 58.4 | 0 |
| 2.0 | 12.8 | 64.8 | 2.5 |
| 5.0 | 8.3 | 65.0 | 2.4 |
| 10.0 | 11.9 | 65.1 | 2.3 |
| 20.0 | 12.9 | 62.0 | 3.5 |

EXAMPLE 5

Effect of reaction conditions. The reactivity of 5% $La_2O_3$/C was investigated under various reaction conditions. From Table 4, it can be seen that the catalyst activity increased significantly from 8.3% to 39.5% when reaction temperature was elevated from 500° C. to 550° C., with slightly decrease in $CF_3I$ selectivity from 65% to 53.6% and slightly increase in $CF_3CF_2I$ selectivity from 2.4% to 5.0%. By increasing the contact time from 19 s to 38 s at 550° C., $CF_3H$ conversion of the catalyst was further increased to 48.3%, with 53.3% $CF_3I$ selectivity and 3.2% $CF_3CF_2I$ selectivity. These data suggested that the catalyst activity was tunable by varying reaction parameters such as reaction temperature and contact time.

TABLE 4

Effect of reaction conditions on the reactivity of 5% $La_2O_3$/C.
Reaction time: $I_2/CF_3H = 0.33$, $O_2/CF_3H = 0.1$. Reaction time: 10 hr.

| Reaction temp. (° C.) | Contact time (s) | $CF_3H$ conversion (%) | $CF_3I$ selectivity (%) | $CF_3CF_2I$ selectivity (%) |
|---|---|---|---|---|
| 500 | 20 | 8.3 | 65.0 | 2.4 |
| 550 | 19 | 39.5 | 53.6 | 5.0 |
| 550 | 38 | 48.3 | 53.3 | 3.2 |

EXAMPLE 6

Effect of promoters/additives on the activity of $La_2O_3$/C. Various promoters/additives can modify the reactivity of $La_2O_3$/C catalyst. Table 4 offers some examples concerning the effect of platinum and potassium. When 1 wt. % Pt was added to 5% $La_2O_3$/C, the catalyst showed longer induction period than that of platinum-free catalyst. Pt—$La_2O_3$/C catalyst gained activity after run for 12 hrs, and its $CF_3H$ conversion and $CF_3I$ selectivity were 9.4% and 62.6%, respectively, after run for 15 hrs (Table 5).

Small amounts of alkali metal salts, such as potassium nitrate, were also added to 5% $La_2O_3$/C and 10% $La_2O_3$/C. The atomic ratio of lanthanum to potassium (La/K) was controlled to be greater than 1 (>1). As can be seen from Table 5, catalyst activity was significantly increased upon addition of small amount of potassium nitrate. The 0.2% K-5% $La_2O_3$/C gave 22.3% $CF_3H$ conversion and 60.9% $CF_3I$ selectivity. With increasing potassium loading, the catalyst activity further increased for both K-5% $La_2O_3$/C and K-10% $La_2O_3$/C. The induction period was reduced by the addition of potassium salt, but the $CF_3CF_2I$ selectivity was higher in the presence of potassium (about 5-6%).

TABLE 5

Reactivity of Pt-5% $La_2O_3$/C, K-5% $La_2O_3$/C, and K-10% $La_2O_3$/C.
Reaction condition: 500° C., $I_2/CF_3H = 0.33$, $O_2/CF_3H = 0.1$,
contact time: 20 s. Reaction time: 10 hr.

| Catalyst | La/K atomic ratio | $CF_3H$ conversion (%) | $CF_3I$ selectivity (%) | $CF_3CF_2I$ selectivity (%) |
|---|---|---|---|---|
| 1.0% Pt-5% $La_2O_3$/C | / | 9.4 (15 hrs) | 62.6 (15 hrs) | 1.7 (15 hrs) |
| 0.2% K-5% $La_2O_3$/C | 6.0 | 22.3 | 60.9 | 5.7 |
| 0.5% K-5% $La_2O_3$/C | 2.4 | 29.3 | 62.5 | 4.6 |
| 1.0% K-5% $La_2O_3$/C | 1.2 | 34.9 | 61.5 | 5.5 |
| 1.0% K-10% $La_2O_3$/C | 2.4 | 40.4 | 58.9 | 6.2 |
| 2.0% K-10% $La_2O_3$/C | 1.2 | 43.6 | 60.3 | 5.8 |

From the above-mentioned examples, it is obvious that catalysts containing elements with $d^1s^1$ configurations and lanthanide are active for making $CF_3I$ and $CF_3CF_2I$. By varying reaction conditions and promoting with other elements, the catalyst activity was further enhanced.

It should also be noted that the terms "first", "second", "third", and the like may be used herein to modify various elements or steps. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. A process for the preparation of a fluoroiodoalkane compound represented by the formula: $CF_3(CF_2)_n$—I, wherein n is 1, comprising:
   contacting A, B and C;
   wherein A is represented by the formula: $CF_3(CF_2)_n$—Y, wherein n is 1, and
      wherein Y is selected from the group consisting of H, Cl, Br, and COOH;
   wherein B is a source of iodine;
   wherein C is a catalyst selected from the group consisting of Sc, Y, Pr, Nd, Pm, Sm, Eu, Gd, Tb, Dy, Ho, Er, Tm, Yb, Lu, mixtures thereof, and salts thereof;
   wherein the contacting is carried out in the presence of a catalyst modifier for the catalyst, and the catalyst modifier is a transition metal element selected from the group consisting of Ti, V, Fe, Zn, Zr, Nb, Tc, Ru, Rh, Pd, Ag, Cd, Hf, Ta, W, Re, Os, Ir, Pt, Au, Hg, salts thereof, and combinations thereof;
   wherein the process occurs at a temperature of from about 100° C. up to about 750° C. and for a contact time sufficient to produce the fluoroiodoalkane compound; and
   wherein the contacting is carried out in the presence of a source of oxygen and in the presence of a diluent selected from the group consisting of nitrogen, helium, argon, CO, $CO_2$, water, organic solvent, and mixtures thereof.

2. The process of claim 1, wherein the catalyst is pretreated at a temperature above or below the reaction temperature using a substance selected from the group consisting of nitrogen, helium, argon, hydrogen, HF, HCl, HI, $F_2$, $Cl_2$, $CF_3H$, $I_2$, air, oxygen, and a mixture thereof.

3. The process of claim 1, wherein the source of iodine is a compound selected from the group consisting of $I_2$, HI, ICl, $IF_5$, $CI_4$, and a mixture thereof.

4. The process of claim 1, wherein the source of oxygen is a compound selected from the group consisting of air, $O_2$, $O_3$, $N_2O$, $H_2O_2$, and a mixture thereof.

5. The process of claim 1, wherein the step of contacting is carried out at a temperature from about 300° C. to about 600° C. and is carried out at a pressure from about 0.001 atm to about 100 atm.

6. The process of claim 1, wherein the catalyst modifier is Pt or a salt thereof.

7. A process for the preparation of a fluoroiodoalkane compound represented by the formula: $CF_3(CF_2)_n$—I, wherein n is 1, comprising:
   contacting A, B and C;
   wherein A is represented by the formula: $CF_3(CF_2)_n$—Y, wherein n is 1, and
      wherein Y is selected from the group consisting of H, Cl, Br, and COOH;
   wherein B is a source of iodine;
   wherein C is a catalyst selected from the group consisting of Sc, Y, Pr, Nd, Pm, Sm, Eu, Gd, Tb, Dy, Ho, Er, Tm, Yb, Lu, mixtures thereof, and salts thereof;
   wherein the contacting is carried out in the presence of a catalyst modifier for the catalyst, and the catalyst modifier is selected from the group consisting of B, Al, Ga, In, Tl, Ge, Sn, Sb, salts thereof, and combinations thereof;
   wherein the process occurs at a temperature of from about 100° C. up to about 750° C. and for a contact time sufficient to produce the fluoroiodoalkane compound; and
   wherein the contacting is carried out in the presence of a source of oxygen and in the presence of a diluent selected from the group consisting of nitrogen, helium, argon, CO, $CO_2$, water, organic solvent, and mixtures thereof.

8. The process of claim 7, wherein the catalyst is pretreated at a temperature above or below the reaction temperature using a substance selected from the group consisting of nitrogen, helium, argon, hydrogen, HF, HCl, HI, $F_2$, $Cl_2$, $CF_3H$, $I_2$, air, oxygen, and a mixture thereof.

9. The process of claim 7, wherein the source of iodine is a compound selected from the group consisting of $I_2$, HI, ICl, $IF_5$, $CI_4$, and a mixture thereof.

10. The process of claim 7, wherein the source of oxygen is a compound selected from the group consisting of air, $O_2$, $O_3$, $N_2O$, $H_2O_2$, and a mixture thereof.

11. The process of claim 7, wherein the step of contacting is carried out at a temperature from about 300° C. to about 600° C. and is carried out at a pressure from about 0.001 atm to about 100 atm.

12. A process for the preparation of a fluoroiodoalkane compound represented by the formula: $CF_3(CF_2)_n$—I, wherein n is 1, comprising:
   contacting A, B and C;
   wherein A is represented by the formula: $CF_3(CF_2)_n$—Y, wherein n is 1, and
      wherein Y is selected from the group consisting of H, Cl, Br, and COOH;
   wherein B is a source of iodine;
   wherein C is a catalyst selected from the group consisting of Sc, Y, Pr, Nd, Pm, Sm, Eu, Gd, Tb, Dy, Ho, Er, Tm, Yb, Lu, mixtures thereof, and salts thereof;
   wherein the contacting is carried out in the presence of a catalyst modifier for the catalyst, and wherein the catalyst modifier is selected from the group consisting of Li, Na, K, Rb, Cs, Be, Mg, Ca, Sr, Ba, salts thereof, and combinations thereof, and wherein the atomic ratio of lanthanide elements to alkali and alkaline earth metals is greater than 1;
   wherein the process occurs at a temperature of from about 100° C. up to about 750° C. and for a contact time sufficient to produce the fluoroiodoalkane compound; and
   wherein the contacting is carried out in the presence of a source of oxygen and in the presence of a diluent selected from the group consisting of nitrogen, helium, argon, CO, $CO_2$, water, organic solvent, and mixtures thereof.

13. The process of claim 12, wherein the catalyst is pretreated at a temperature above or below the reaction temperature using a substance selected from the group consisting of nitrogen, helium, argon, hydrogen, HF, HCl, HI, $F_2$, $Cl_2$, $CF_3H$, $I_2$, air, oxygen, and a mixture thereof.

14. The process of claim 12, wherein the source of iodine is a compound selected from the group consisting of $I_2$, HI, ICl, $IF_5$, $CI_4$, and a mixture thereof.

15. The process of claim 12, wherein the source of oxygen is a compound selected from the group consisting of air, $O_2$, $O_3$, $N_2O$, $H_2O_2$, and a mixture thereof.

16. The process of claim 12, wherein the step of contacting is carried out at a temperature from about 300° C. to about 600° C. and is carried out at a pressure from about 0.001 atm to about 100 atm.

17. The process of claim 12, wherein the catalyst modifier is K or a salt thereof.

* * * * *